United States Patent [19]
Bitonti et al.

[11] Patent Number: 5,214,050
[45] Date of Patent: May 25, 1993

[54] ESTERS OF CASTANOSPERMINE IN THE TREATMENT OF CEREBRAL MALARIA

[75] Inventors: Alan J. Bitonti, Maineville, Ohio; Peter P. McCann, Lebanon, Ind.; Albert Sjoerdsma, Cincinnati, Ohio

[73] Assignee: Merrell Dow Pharmaceuticals Inc., Cincinnati, Ohio

[21] Appl. No.: 846,656

[22] Filed: Mar. 5, 1992

Related U.S. Application Data

[63] Continuation-in-part of Ser. No. 422,869, Oct. 17, 1989, abandoned.

[51] Int. Cl.$^5$ .................... A01N 43/42; A61K 31/44
[52] U.S. Cl. .................................................... 514/299
[58] Field of Search ........................................ 514/299

[56] References Cited

FOREIGN PATENT DOCUMENTS 0297534  1/1989  European Pat. Off. .
0309952  4/1989  European Pat. Off. .

Primary Examiner—Nathan M. Nutter
Attorney, Agent, or Firm—Neal O. Willmann

[57] ABSTRACT

Red blood cells which are infected with the parasite P. falciparum cause the cells to become sticky and less deformable. This results in a build-up of cells on the vascular wall and creates occlusions to blood flow which are thought to cause the cerebral, renal and liver complications of P. falciparum infections. Certain esters of castanospermine prevent or reduce the adhesion of falciparum infected blood cells to the vascular endothelial wall and are a useful adjunct in the treatment of malaria.

1 Claim, No Drawings

ESTERS OF CASTANOSPERMINE IN THE TREATMENT OF CEREBRAL MALARIA

This is a continuation-in-part of application Ser. No. 07/422,869, filed Oct. 17, 1989, and now abandoned.

Malarial infections are responsible for more than a million deaths annually and more than 100 million cases are believed to occur each year. In particular, infections of the *Plasmodium falciparum* organism, i.e. falciparum malaria, are the most difficult to treat and are also the most common. Cerebral malaria is a common side effect of Falciparum malaria infection and is frequently fatal. Cerebral malaria is characterized by consciousness disturbances, behavioral changes, hallucinations, motor seizures, meningismus, and tremors.

Cell membranes of red blood cells infected with the falciparum parasite undergo modifications and become less deformable and more adherent to vascular endothelium. In untreated and inadequately treated disease, intravascular accumulation of infected cells results in restricted capilary blood flow. The resultant disturbance in microcirculation causes oxygen deprivation in certain tissues and is believed to give rise to the serious and frequently fatal complications of falciparum malaria including renal failure, pulmonary edema, and cerebral malaria.

Therapy of human infections of other Plasmodium species, *P. ovale, P. vivax* and *P. malariae*, is also complicated by the occurrence of similar microcirculation disturbances.

Applicants have discovered that certain esters of castanospermine prevent or reduce the adhesion of Plasmodium infected blood cells to the vascular endothelial wall. Such compounds will, therefore, be a useful adjuvant in the treatment of Plasmodium malaria, particularly in those cases where microcirculation complications occur.

SUMMARY OF THE INVENTION

Castanospermine esters of the formula

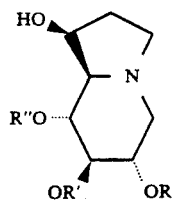

wherein R, R' and R" are independently hydrogen, $C_{1-18}$ alkanoyl, $C_{3-18}$ alkenoyl, (R''''-X-)($C_{2-18}$ alkanoyl), ($C_{1-4}$ alkoxy)—CO—$(CH_2)_n$—CO—:

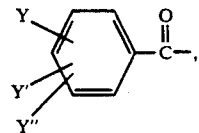

n is a whole number from 0 to 4; Y is hydrogen, $C_{1-4}$ alkyl, phenyl, $C_{1-4}$ alkoxy; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; Ac is benzoyl or $C_{2-6}$ alkanoyl; R'''' is hydrogen or $C_{1-4}$ alkyl; X is O, S or NH; with R, R', and R" selected in such a way that at least one of them but not all three of them are hydrogen; or the pharmaceutically acceptable salts of the aforesaid compounds are useful in the prevention of microcirculation disturbances which accompany Plasmodium malaria infections. The formula 1 compounds are useful in the treatment of cerebral malaria.

DETAILED DESCRIPTION OF THE INVENTION

The $C_{1-18}$ alkanoyl groups referred to above can be straight- or branched-chain and can be exemplified by formyl, acetyl, propionyl, butyryl, isobutyryl, hexanoyl, octanoyl, decanoyl and hexadecanoyl. $C_{2-18}$ Alkanoyl is defined similarly except it does not include formyl. $C_{3-18}$ alkenoyl is defined to be a straight or branched chain alkene group having 3 to 18 carbon atoms and having one to three carboncarbon double bonds of cis or trans geometry. Examples are methacryloyl, sorboyl, acroloyl, 2-butenoyl, linolenoyl, linoleoyl, and oleoyl.

$C_{8-18}$ alkenoyl is defined similarly except that the group has from 8 to 18 carbon atoms. $0,.C_{12-18}$ alkanoyl is also defined similarly except that the group has from 12 to 18 carbon atoms. Examples of (R''''—X—)($C_{2-18}$ alkanoyl) groups are 3-hydroxypropanoyl, 3-mercaptopropanoyl, 2-butoxypropanoyl, 2-(methylthio)propanoyl and 2-aminobutanoyl. The group ($C_{1-4}$ alkoxy)—CO—$(CH_2)_n$—CO— describes an acyl group derived from an alkanedicarboxylic acid containing n+2 carbon atoms and having one of the acid groups esterified with an alkyl group containing from 1 to 4 carbon atoms. The halogens referred to above can be exemplified by fluorine, chlorine, bromine or iodine. The $C_{2-6}$ alkanoyl groups referred to above (Ac) can be exemplified by acetyl, propionyl, butyryl, isobutyryl, and hexanoyl. The $C_{1-4}$ alkyl groups referred to above, whether alone or as part of an alkoxy, an alkylsulfonyl or an alkylmercapto or some other group, can be straight- or branched-chain alkyl groups containing up to 4 carbon atoms. Examples of various such groups are methyl, ethyl, propyl, butyl, methoxy, ethoxy, butoxy, methylsulfonyl, ethylsulfonyl, methylmercapto and ethylmercapto. The phenyl($C_{2-6}$ alkanoyl) groups referred to above can be exemplified by benzeneacetyl and benzenepropionyl.

Acid addition salts with pharmaceutically acceptable acids referred to above are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Preferred compounds of the present invention are those wherein R, R', and R" are each independently a $C_{1-18}$ alkanoyl, $C_{3-18}$ alkenoyl group, or a

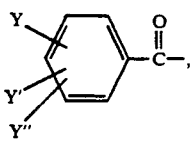

wherein Y is a hydrogen, $C_{1-4}$ alkyl, $C_{1-4}$ alkoxy, or phenyl and wherein Y' and Y" are each a hydrogen. More preferred are those compounds of formula 1 wherein R" is a hydrogen and wherein one of R or R' is a hydrogen and the other is a $C_{1-18}$ alkanoyl, $C_{3-18}$ alkenoyl group, or a

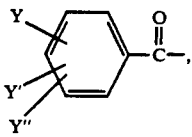

wherein Y' and Y" are each a hydrogen and wherein Y is a hydrogen or a $C_{1-4}$ alkyl. Even more preferred are those compounds of formula 1 wherein R' and R" are each a hydrogen and wherein R is a $C_{1-18}$ alkanoyl, especially a straight chain $C_{1-18}$ alkanoyl, $C_{3-18}$ alkenoyl group, especially a straight chain $C_{8-18}$ alkenoyl, or a

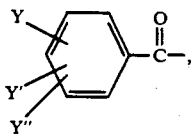

wherein Y' and Y" are each a hydrogen and wherein Y is a hydrogen or a methyl. Most preferred are those compounds of formula 1 wherein R' and R" are each a hydrogen and wherein R is a propylcarbonyl, butylcarbonyl, a straight chain $C_{12-18}$ alkenoyl, particularly oleoyl, a benzoyl or a p-methylbenzoyl.

The esters of the present invention are prepared by the reaction of castanospermine with an appropriate acid chloride or anhydride in an inert solvent. The halide can be a chloride or bromide; the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited excess of the acid derivative (halide or anhydride) is used, which would mean that up to about a threefold excess of the acylating agent is used. Use of a solvent in relatively large amounts serves to dilute the reactants and hold down the amount of higher acylated products that form. The solvent used is preferably one that will dissolve the reactants used without reacting with them. It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the amount of acylation that takes place. Preferably, the reaction is carried out with cooling in an ice-bath for a period of about 16 hours to give the monoesters with the reaction time extended to a longer period, such as 7 days, if diesters are desired. The reaction can actually be carried out at higher temperatures and, in fact, heating can be used as long as the various factors involved are properly controlled. The fact of the matter is, when the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important when the reaction is carried out under conditions which would favor the isolation of monoesters.

The procedures as described above will generally give 6- or 7-monoesters or 6,7- or 6,8-diesters. Other isomers can be obtained by the appropriate use of blocking groups which can be removed readily and selectively. In addition, it would also be possible to use the blocking groups in a series of reactions which would give, with greater specificity, some of the compounds that can also be obtained directly. Some examples of blocking groups which are useful in such procedures are 2-(dibromomethyl)benzoyl esters and 2-iodobenzoyl esters. 1,8-Ketals of castanospermine such as 1,8-O-isopropylidenecastanospermine and 1,8-O-cyclohexylidenecastanospermine can also be used. In addition, alkanoyl groups, preferably those containing 2 to 6 carbon atoms, can be used as blocking groups in the preparation of benzoate and substituted benzoate esters as the members of the former group are preferentially removed by acid treatment.

The use of such blocking groups can be illustrated as follows. Thus, castanospermine can be reacted with 2-(dibromomethyl)benzoyl chloride to give the 6,7-diester. This diester is then further reacted with an appropriate acid halide or anhydride, corresponding to the ester group desired in the final product, to give the castanospermine compound which is thus further esterified at the 8-hydroxy group. The two (dibromomethyl)benzoyl protecting groups are then readily removed by first converting the dibromomethyl substituents to formyl groups (using silver perchlorate and 2,4,6-collidine in aqueous acetone) followed by hydrolysis of the resulting formylbenzoic acid ester groups using morpholine and hydroxide ion to give the castanospermine compound having free hydroxy groups at the 6- and 7-positions and monoesterified at the 8-position with the desired ester group. The indicated procedure can be used in a similar way, proceeding through a 6-[2-(dibromomethyl)benzoyl] monoester, to give the 7,8-diester isomer.

The use of 2-(dibromomethyl)benzoate esters in selective esterification procedures such as those referred to above is described by Chattopadhyaya et al., J.C.S. Chem. Comm., 1979, 987. From the above article and other references cited therein, the specific manner in which the 2-(dibromomethyl)benzoyl ester group can be used as a selective protecting group should be clear to one skilled in the art. The indicated ester group is useful as a selective protecting group because of the fact that it can be readily converted to the corresponding 2-formylbenzoyl ester. Such a 2-formyl ester is then hydrolyzed readily under mild conditions by an intramolecular reaction as described in the article referred to above. Obviously, such an ester would be special and would be clearly distinguished from most esters which require much stronger conditions (i.e., heating in the presence of base or acid) to effect hydrolysis and are only hydrolyzed under such stronger conditions. Thus, when a 2-formylbenzoate is present in a molecule with other ester groups and the compound is subjected to the mild hydrolysis conditions described earlier, only the formylbenzoate would be affected. In particular, no other substituted benzoate ester would be affected in a similar manner.

As far as 2-iodobenzoyl esters are concerned, their use as selectively removable blocking groups would be similar to the use of the 2-(dibromomethyl)benzoyl esters discussed above except that a differenc procedure would be used to selectively remove the 2-iodobenzoyl esters. Thus, castanospermine would be reacted with 2-iodobenzoyl chloride to give a mono- or di-ester as desired and this would be further reacted with an appropriate acid halide or anhydride corresponding to the ester group desired in the final product. The iodobenzoyl group or groups are then removed by standard chlorination/aqueous bicarbonate oxidation of the iodo to iodosyl to give 2-iodosobenzoic acid (after acidification) and the castanospermine derivative having a free hydroxy group at the positions previously occupied by the iodobenzoyl ester. This procedure for using iodobenzoyl esters as protecting groups is described by Moss et al., *Tetrahedron Letters*, 28, 5005 (1987).

The use of alkanoyl groups as blocking groups can be illustrated as follows. Castanospermine 6-butyrate is prepared using 1,8-O-isopropylidenecastanospermine by the general procedure described in the preceding paragraph. The 6-butyrate is then reacted with an acid halide such as benzoyl chloride to give a mixture of castanospermine 1-benzoate 6-butyrate and castanospermine 8-benzoate 6-butyrate. The mixture of diesters is then treated with an equivalent of an acid such as hydrogen chloride in methanol whereupon the butyrate ester group is hydrolyzed without affecting the benzoate ester group because butyrate esters are hydrolyzed much more readily under these conditions. The resulting mixture of castanospermine 1-benzoate and 8-benzoate is then separated by standard procedures such as chromatography to give the individual pure isomers.

To prepare those compounds of the present invention wherein R'''' is hydrogen and those compounds wherein X is NH, the appropriate benzyl substituted or benzyloxycarbonyl substituted (i.e., benzyloxy, benzylthio or benzyloxycarbonylamino) alkanoyl chloride is used in a procedure as described above and then the benzyl group or benzyloxycarbonyl group is removed by standard procedures (i.e., catalytic hydrogenation).

The compounds of formula 1 reduce the adhesion of falciparum infected blood cells to the vascular endothelial wall. This can be demonstrated by measuring the binding of *P. falciparum*-infected erythrocytes to formalin-fixed endothelial cells and amelanotic melanoma cells by the method of Udeninya, et al., *J. Protozool.*, Vol. 32(1) 1985. The results of such testing on representative compounds of formula 1 are reported as percentage of control in Table 1.

TABLE 1

INHIBITION OF BINDING OF INFECTED ERYTHROCYTES TO HUMAN MELANOMA CELLS IN VITRO

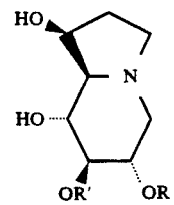

| R | R' | Effect at 25 μm as a percentage of control |
|---|----|---|
| $CH_3(CH_2)_8CO-$ | H | 59 |
| H | $CH_3(CH_2)_2CO-$ | 26 |
|   |   | (38 at 10 μM) |
| $CH_3(CH_2)_4CO-$ | H | 44 |
|   |   | 32 at 10 μM |
| $CH_3(CH_2)_3CO-$ | H | 27 |
|   |   | (30 at 10 μM) |
| $CH_3CH(CH_3)CO-$ | H | 78 |
| $CH_3(CH_2)_{14}CO-$ | H | 50 |
| H | $C_6H_5CO-$ | 92 |
| $pCH_3OC_6H_4CO-$ | H | 43 |
| $pCH_3C_6H_4CO-$ | H | 25 |
|   |   | (69 at 10 μM) |
| oleoyl | H | 7 |
|   |   | (38 at 1 μM) |

Human melanoma cells grown on plastic overslips were incubated with test compounds for 72 hours prior to addition of erythrocytes infected with the ItG strain of *P. falciparum*. Binding between the infected erythrocytes and the melanoma cells took place during a 60 minute incubation at 37° C. Unbound erythrocytes were washed free and the melanoma cells and attached erythrocytes were stained with Giemsa and the number of attached erythrocytes per 100 melanoma cells was determined under 400 × magnification.

The compounds of formula 1 are useful in the treatment of the microcirculation complications characteristic of those individuals infected with the parasite *Plasmodium falciparum*, *Plasmodium ovale*, *Plasmodium vivax* and *Plasmodium malariae*, that is, the compounds of formuala 1 prevent or lessen the severity of such Plasmodium side effects as cerebral malaria and other complications resulting from microcirculation disturbances. Cerebral malaria is characterized by consciousness disturbances, behavioral changes, hallucinations, motor seizures, meningismus, and tremors. Other side effects of Plasmodium infections include renal failure and pulmonary edema.

The amount of the castanospermine ester derivative of formula 1 to be administered can vary widely according to the particular dosage unit employed, the period and frequency of treatment, the age and sex of the patient treated, the nature and extent of the disorder treated, and the particular castanospermine ester derivative selected. Moreover the castanospermine ester derivative can be used in conjunction with other agents known to be useful in the treatment of Plasmodium infections such as various quinoline derivatives, for example, quinine, chloroquine, primaquine, sulfadoxine, mefloquine, and pyrimethamine. The expression "in conjunction with" indicates that the formula 1 castanospermine ester can be administered in a single dosage form together with the antimalarial agent or in separate dosage forms. Concurrent administration of a formula 1 ester with an antimalarial agent is not intended. Conjunctive administration includes the administration of a formula 1 ester substantially prior to or subsequent to administration of an antimalarial agent. The amount of a castanospermine ester derivative of formula 1 effective to prevent or reduce the adhesion of falciparum infected blood cells to the vascular endothelial wall and to treat the side effects of Plasmodium infections including cerbral malaria will generally range from about 15 mg/kg to 500 mg/kg. A unit dosage may contain from 25 to 500 mg of the castanospermine ester derivative, and can be taken one or more times per day. The castanospermine ester derivative can be administered with a pharmaceutical carrier using conventional dosage unit forms either orally or parenterally.

The preferred route of administration is oral administration. For oral administration the castanospermine ester derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The castanospermine ester derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the castanospermine ester derivative of formula 1 in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLE 1

[1S-(1α,6β,7α,8β,8aβ)]octahydro-1,6,7,8-indolizinetetrol-6-benzoate

A slurry of 4.0 g of castanospermine in 140 ml of pyridine was stirred at room temperature for 30 minutes until essentially all of the solids had dissolved. The solution was cooled to 0° C. in an ice/water bath, and a solution of 5.85 ml of benzoyl chloride in 15 ml of pyridine was added dropwise over 15 minutes under nitrogen. After the addition, the reaction was stirred at 8° C. overnight.

The reaction mixture was partitioned between 225 ml methylene chloride and 300 ml water. The organic layer was separated and the aqueous layer extracted with two 225-ml portions of methylene chloride. The combined organic layers were washed successively with 150 ml of 0.5N hydrochloric acid, saturated sodium carbonate, water and saturated sodium chloride solutions, and then dried over sodium sulfate. Evaporation of solvents under reduced pressure gave 2.9 g of a tan glassy residue.

This material was slurried in chloroform and a white precipitate formed. These solids were isolated to afford 910 mg of a white powder. Thin layer chromatography (85:15, ethyl:methanol) analysis showed the material to be composed of two components (Rf 0.33 and Rf 0.26). The solid mixture was slurried in 45 ml of 4:1 ethyl acetate:methanol and filtered. The residue was dried in vacuo to provide 350 mg of [1S-(1α,6β,7α,8β,8aβ)]-octahydro-1,6,7,8-indolizinetetrol 6-benzoate as a white powdery solid melting at about 233°–236° C., with decomposition. This corresponded to the less polar component of the mixture. NMR (DMSO-$d_6$) $\delta$1.5–2.2 (m, 5H), 2.9–3.6 (m, 4H), 4.1 (m, 1H, $C_1$—H), 4.3 (d, 1H, —OH) 4.7 (d, 1H, —OH), 4.8 (sextet, 1H, $C_6$—H), 5.1 (d, 1H, —OH), 7.6–8.1 (m, 5H, aryl). MS (CI—$CH_4$) 294 (MH+), 276 (MH+-$H_2O$), 172 (MH+—$PhCO_2H$).

The filtrate from above was condensed and fractionated by preparative thin layer chromatography (silica gel, 80:20, ethyl acetate:methanol) to provide 120 mg of the more polar component, [1S-(1α,6β,7α,8β,8aβ)]-octahydro-1,6,7,8-indolizinetetrol 7-benzoate as a white powdery solid melting at about 200°–202° C. NMR (DMSO-d$_6$+D$_2$O) 1.5–2.2 (m, 5H), 2.9–3.1 (m, 2H), 3.6–3.8 (m, 2H), 4.1 (m, 1H, C$_1$—H), 4.8 (t, 1H, C$_7$—H), 7.4–8.1 (m, 5H, aryl). MS (CI—CH$_4$) 294 (MH+), 276 (MH+—H$_2$O), 172 (MH+—PhCO$_2$H).

EXAMPLE 2A

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0°–4° C. for 7 days. Water, 10 ml, was added and the mixture was evaporated to dryness in vacuo. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf=0.42 and Rf=0.11). The mixture was separated by preparative high pressure liquid chromatography (silica gel, 1:1 ethyl acetate:hexane) to provide 1.9 g (48%) of the more polar [1S-(1α,6β,7α,8β,8aβ)]-octahydro-1,6,7,8-indolizinetetrol 6,7-dibenzoate as a dry foam melting at about 79°–81° C. NMR (DMSO-d$_6$/D$_2$O) δ1.5–2.3 (m, 5H), 3.0–3.4 (m, 2H), 3.9 (t, 1H), 4.2 (m, 1H, C$_1$—H), 5.15 (m, 1H, C$_6$—H), 5.3 (t, 1H, C$_7$—H), 7.4–8.0 (m, 10H, aryl). MS (FAB-Xe) 398 (MH+), 380 (MH+—H$_2$O), 276 (MH+—PhCO$_2$H). The less polar component (Rf=0.42) was isolated as a dry foam melting at about 75°–78° C. which was [1S-(1α,6β,7α,8β,8aβ)]-octahydro-1,6,7,8-indolizinetetrol 6,7,8-tribenzoate.

EXAMPLE 2B

Castanospermine (38 g) was added to 250 ml of pyridine and the mixture was cooled at 0° C. while 27.9 g of benzoyl chloride was added dropwise. After this addition was complete, the mixture was stirred at room temperature for 4 hours and then cooled again to 0° C. An additional 27.9 g of benzoyl chloride was added and the mixture was stirred at room temperature for 6 days. After dilution with 20 ml of water, the mixture was evaporated to dryness in vacuo to leave a syrupy golden residue which was stirred vigorously with 100 ml of 3N hydrochloric acid and 400 ml of methylene chloride. The white amorphous solid which formed was [1S-(1α,6β,7α,8β,8aβ)]-octahydro-1,6,7,8-indolizinetetrol 6,7-dibenzoate hydrochloride and this was separated by filtration and dried.

EXAMPLE 3

When the procedure of Example 1 was repeated using castanospermine and the appropriate acid chloride, the following compounds were obtained:

[1S-(1α,6β,7α,8β,8aβ)]-octahydro-1,6,7,8-indolizinetetrol 6-(4-fluorobenzoate) melting at about 216°–218° C.

[1S-(1α,6β,7α,8β,8aβ)]-octahydro-1,6,7,8-indolizinetetrol 7-(4-fluorobenzoate) melting at about 190°–193° C.

[1S-(1α,6β,7α,8β,8aβ)]-octahydro-1,6,7,8-indolizinetetrol 7-(2,4-dichlorobenzoate) melting at about 179°–181° C.

[1S-(1α,6β,7α,8β,8aβ)]-octahydro-1,6,7,8-indolizinetetrol 6-(4-bromobenzoate) melting at about 234°–235° C.

[1S-(1α,6β,7α,8β,8aβ)]-octahydro-1,6,7,8-indolizinetetrol 7-(4-bromobenzoate) melting at about 199°–202° C.

[1S-(1α,6β,7α,8β,8aβ)]-octahydro-1,6,7,8-indolizinetetrol 6-(4-methoxybenzoate) melting at about 221°–224° C.

EXAMPLE 4

When the procedure of Example 2 was repeated using castanospermine and 4-fluorobenzoyl chloride, the product obtained was [1S-(1α,6β,7α,8β,8aβ)]-octahydro-1,6,7,8-indolizinetetrol 6,7-bis(4-fluorobenzoate) melting at about 82°–84° C.

EXAMPLE 5

To a suspension of 3 g of castanospermine in 30 ml of pyridine at 0° C. was added dropwise a solution of 3 g of 4-methylbenzoyl chloride. After the addition, the mixture wad allowed to warm to room temperature and then heated at 55° C. for 24 hours. The reaction mixture was diluted with 10 ml of water and evaporated to dryness in vacuo. The resulting residue was stirred in 150 ml of a 1:2 mixture of water:methylene chloride. The insoluble material was separated by filtration to provide an amorphous off-white solid which was dissolved in 60 ml of hot methanol, treated with 0.5 g of activated charcoal and filtered. The colorless filtrate was cooled to give colorless crystals of [1S-(1α,6β,7α,8β,8aβ)]-octahydro-1,6,7,8-indolizinetetrol 6-(4-methylbenzoate) melting at about 255°–258° C. with decomposition (580 mg, 12% yield).

The two-phase water/methylene chloride mixture obtained above was evaporated to dryness and the residue was dissolved in 50 ml of a 1:2 mixture of methanol:ethyl acetate. The solution was fractionated by preparative high pressure liquid chromatography (silica gel, 9:1 ethyl acetate: methanol) and fractions containing the more polar component (i.e., more polar than the 6-ester obtained in the preceding paragraph) were collected and evaporated in vacuo to provide a colorless solid which was [1S-(1α,6β,7α, 8β,8aβ)]-octahydro-1,6,7,8-indolizinetetrol 7-(4-methylbenzoate) melting at about 220°–223° C. with decomposition (210 mg, 4% yield).

EXAMPLE 6

When the procedure of Example 5 was repeated using castanospermine and the appropriate acid chloride, the following esters were obtained:

6-(2-Methylbenzoate) melting at about 213°–215° C.,
6-(3-Methylbenzoate) melting at about 212° C. with decomposition,
6-(2-Thiophenecarboxylate) melting at about 214°–215° C.,
6-(2-Furancarboxylate) melting at about 209°–212° C.

In addition, when the procedure of Example 5 is repeated using castanospermine and the appropriate acid chloride, the following esters are obtained:
6-Hexadecanoate,
6-Methoxalate,
6-(3-Ethoxycarbonyl)propionate,
7-(3-Methylbenzoate),
6-(3-Trifluoromethylbenzoate), 6-(4-Methylsulfonylbenzoate),
6-(4-Methylmercaptobenzoate),
6-(3-Cyanobenzoate),
6-(4-Dimethylaminobenzoate),
6-(3,4-Methylenedioxybenzoate),
6-(3,4,5-Trichlorobenzoate),
7-(3,4,5-Trichlorobenzoate),
6-(2,4-Dimethylbenzoate),
6-(2-Carbomethoxybenzoate),
6-(Benzeneacetate),
7-(Benzeneacetate),
6-(4-Chlorobenzeneacetate),
6-(Benzenepropionate).

EXAMPLE 7

Castanospermine (350 mg) was added to 5 ml of pyridine and stirred under nitrogen at room temperature. Butyric anhydride (0.97 g) was added dropwise and the mixture was kept at room temperature for 24 hours. The reaction mixture was evaporated to dryness in vacuo to leave a syrupy residue. The residue was dissolved in ether and a colorless solid precipitated when pentane was added. Recrystallization of the solid from a mixture of ether and petroleum ether gave colorless needles of [1S-(1α,6β,7α,8β,8aβ)]-octahydro-1,6,7,8-indolizinetetrol 6,8-dibutanoate melting at about 110°–111° C. (22 mg, 4% yield). NMR (CDCl$_3$) δ3.7 (t, 1H, C$_7$—H), 4.1 (m, 1H, C$_1$—H), 4.85 (t, 1H, C$_8$—H), 5.0 (m, 1H, C$_6$—H). MS (CI—CH$_4$) 330 (MH$^+$), 312 (MH$^+$—H$_2$O).

EXAMPLE 8

When the procedure of Example 7 is repeated using acetic anhydride, propionic anhydride or caproic anhydride in place of the butyric anhydride, the corresponding 6,8-diesters are obtained.

EXAMPLE 9

To a stirred suspension of 1.5 g of castanospermine in 15 ml of pyridine cooled at 0° C. in an ice-bath was added dropwise 1.0 g of butyryl chloride. The mixture was stirred at room temperature for 3 days and added to a 1:1 mixture of water:methylene chloride (400 ml). After partitioning, the aqueous phase was concentrated in vacuo to provide an oily residue which was fractionated by radial thin layer chromatography (silica gel, 2 mm thickness plate, 2:8 methanol:chloroform) to provide 68 mg of [1S-(1α,6β,7α,8β,8aβ)]-octahydro-1,6,7,8-indolizinetetrol 6-butanoate, homogeneous by thin layer chromatography (silica gel, 2:8 methanol:chloroform, Rf=0.5). Recrystallization of the product from 5:95 isopropanol:hexane gave a colorless solid melting at 113°–114° C. NMR (CDCl$_3$) δ3.5–3.8 (2t, 2H, C$_7$—H and C$_8$—H), 4.4 (m, 1H, C$_1$—H), 4.95 (m, 1H, C$_6$—H). MS (CI—CH$_4$) 260 (MH$^+$), 242 (MH$^+$—H$_2$O), 172 (MH$^+$-C$_3$H$_7$CO$_2$H).

Similarly, when the above procedure was repeated using acetyl chloride or propionyl chloride, the following monoesters were obtained:

[1S-(1α,6β,7α,8β,8aβ)]-octahydro-1,6,7,8-indolizinetetrol 6-acetate melting at about 188°–189° C.
[1S-(1α,6β,7α,8β,8aβ)]-octahydro-1,6,7,8-indolizinetetrol 7-propionate melting at about 153°–155° C.

EXAMPLE 10

Castanospermine (0.38 g) was added to a stirred solution of 5 ml of pyridine and cooled in an ice bath. Benzoyl chloride, 0.96 g, was added dropwise to the mixture and the resulting suspension was kept at 0°–4° C. for 18 hours. Ice water, 5 ml, was added and the mixture was diluted with 50 ml of ether. The ethereal solution was separated and washed with 1N hydrochloric acid (2×50 ml), saturated aqueous sodium bicarbonate solution (50 ml) and brine (50 ml). The organic phase was dried with anhydrous magnesium sulfate and evaporated to dryness in vacuo. The resulting residue was redissolved in 3 ml of ether and shown to be a mixture of two major components by thin layer chromatography (6:4 ether:hexane, silica gel, R$_f$=0.35; 0.20). The mixture was separated by preparative thin layer chromatography (silica gel, 6:4 ether:hexane) to provide 0.30 g (30%) of the less polar (R$_f$=0.35) [1S-(1α,6β,7α,8β,8aβ)]-octahydro-1,6,7,8-indolizinetetrol 1,6,8-tribenzoate as a dry, foamy solid melting at about 85°–87° C. NMR (CDCl$_3$/D$_2$O) δ1.7–2.6 (m, 5H), 3.0–4.1 (m, 3H), 5.1–5.7 (m, 3H), 7.1–8.2 (m, 15H, aryl). MS (CI—NH$_3$) 502 (MH$^+$), 380 (MH$^+$—PhCO$_2$H). The more polar component (R$_f$=0.20) was isolated as a dry foam melting at about 75°–78° C. and was [1S-(1α,6β,7α,8β,8a8)]-octahydro-1,6,7,8-indolizinetetrol 6,7,8-tribenzoate.

EXAMPLE 11

A mixture of 5.0 g of [1S-(1α,6β,7α,8β,8a8)]-octahydro-1,6,7,8-indolizinetetrol 6,7-dibenzoate hydrochloride, 100 ml of 1,2-dimethoxyethane, 22 ml of 2-methoxypropene and 0.22 g of 4-toluenesulfonic acid monohydrate was refluxed with stirring for 1.5 hours to give a clear solution. The reaction was cooled to 25° C. and diluted with 30 ml of saturated aqueous sodium bicarbonate solution and 60 ml of water. This solution was then extracted twice with methylene chloride and the combined organic extracts were dried over magnesium sulfate and the solvent was evaporated in vacuo to give a light green foam. This material was recrystallized from pentane to give [1S-(1α,6β,7α,8β,8aβ)]-1,8-O-isopropylideneoctahydro-1,6,7,8-indolizinetetrol 6,7-dibenzoate as white crystals melting at about 132°–133° C. (78.6% yield).

To a solution of 0.34 g of [1S-(1α,6β,7α,8β,8aβ)]-1,8-O-isopropylideneoctahydro-1,6,7,8-indolizinetetrol 6,7-dibenzoate in 50 ml of tetrahydrofuran, at 25° C., there was added 3.1 ml of 1N aqueous sodium hydroxide in one portion. The reaction mixture was stirred for 24 hours, diluted with 10 ml of saturated brine, and extracted with four portions of methylene chloride. The combined organic extracts were dried with magnesium sulfate and the solvent was evaporated in vacuo to give [1S-(1α,6β,7α,8β,8aβ)]-1,8-O-isopropylideneoctahydro-1,6,7,8-indolizinetetrol as a clear glass which was used without further purification (95% yield). 1H NMR (CDCl3, 300 MH$_2$) δ4.5 (d, 1H), 3.8 (m, 1H), 3.65 (t, 1H), 3.5 (dd, 1H), 3.25 (dd, 1H), 3.0 (m, 2H), 2.8 (m, 2H), 2.2 (m, 1H), 1.9 (m, 1H).

EXAMPLE 12

A mixture of 0.3 g of [1S-(1α,6β,7α,8β,8aβ)]-1,8-O-isopropylideneoctahydro-1,6,7,8-indolizinetetrol, 6.0 ml of methylene chloride and 0.54 ml of triethylamine was cooled to 0° C. and 0.18 ml of benzoyl chloride was added dropwise with stirring. The reaction was then stirred at 0°–5° C. for 24 hours before dilution with 10 ml of water and 3 ml of saturated aqueous sodium bicarbonate solution. The layers were separated and the aqueous layer was extracted twice with methylene chloride. The combined organic layers were then dried over magnesium sulfate and the solvent was evaporated in vacuo to give a crude solid product. This solid was recrystallized from ethyl acetate/pentane (1:2) to give [1S-(1α,6β,7α,8β,8aβ)]-1,8-O-isopropylideneoctahydro-1,6,7,8-indolizinetetrol 6-benzoate as white needles melting at about 181°-183° C. (77.9% yield).

A solution was prepared from 0.2 g of [1S-(1α,6β,7α,8β, 8aβ)]-1,8-O-isopropylideneoctahydro-1,6,7,8-indolizinetetrol 6-benzoate and 10 ml of methanol. To this solution, at 25° C., was added 0.34 g of 4-toluenesulfonic acid monohydrate in one portion. The reaction was stirred for one hour and the mixture was then diluted with 30 ml of methylene chloride, 10 ml of saturated aqueous sodium bicarbonate solution, and 10 ml of saturated brine. The layers were separated, the aqueous layer was extracted five times with methylene chloride, and the combined organic layers were dried over magnesium sulfate. The solvent was then evaporated in vacuo to give [1S-(1α,6β,7α,8β,8aβ)]-octahydro-1,6,7,8-indolizinetetrol 6-benzoate as a white powder melting at about 233°-235° C. with decomposition (91% yield).

EXAMPLE 13

A suspension of 4 g of [1S-(1α,6β,7α,8β,8aβ)]-1,8-O-isopropylideneoctahydro-1,6,7,8-indolizinetetrol 6,7-dibenzoate hydrochloride in 100 ml of chloroform was stirred vigorously with 150 ml of saturated aqueous sodium bicarbonate for 30 minutes. The organic layer was separated and dried over magnesium sulfate and the solvent was evaporated in vacuo to give a syrup which crystallized to give solid [1S-(1α,6β,7α,8β,8aβ)]-1,8-O-isopropylideneoctahydro-1,6,7,8-indolizinetetrol 6,7-dibenzoate upon the addition of 40 ml of methanol. The resultant slurry was then stirred and two drops of 25% sodium methoxide in methanol was added; stirring was continued at room temperature for 3 days. The solvent was then evaporated from the mixture in vacuo and the residual solid was redissolved in 100 ml of chloroform. Three equivalents of triethylamine was added followed by the dropwise addition of 1-2 equivalents of 2-furancarbonyl chloride and the resulting mixture was stirred at room temperature for 24 hours.

The crude reaction mixture obtained above was diluted with 20 ml of water and 6 ml of saturated aqueous sodium bicarbonate solution. The layers were mixed thoroughly and then separated. The aqueous phase was extracted twice with methylene chloride and the combined organic layers were dried over magnesium sulfate. The solvent was then evaporated to leave a brown syrup. This syrupy residue was applied to a silica gel column and eluted with ethyl acetate. The fractions containing the desired product were combined and the solvent was evaporated in vacuo to provide a yellowish syrup which crystallized on standing. A portion of this product was dissolved in 10 ml of methanol at room temperature and 0.20 g of 4-toluenesulfonic acid hydrate was added. The resultant solution was first stirred under nitrogen at room temperature for two hours and then heated at reflux for two hours. The resulting mixture was dissolved in methanol/ethyl acetate (1:4) and applied to a silica gel column and the column was eluted with methanol/ethyl acetate (1:9). The fractions containing the desired product were combined and the solvent was evaporated to leave a residue which crystallized on standing to give slightly off-white plates of [1S-(1α,6β,7α,8β, 8aβ)]-octahydro-1,6,7,8-indolizinetetrol 6-(2-furancarboxylate) malting at about 209°-212° C.

What is claimed is:

1. A method of treating cerebral malaria by reducing the adhesion of Plasmodium species infected blood cells to the vascular endothelial wall in a patient in need thereof which comprises intravenously administering to the patient a therapeutically effective amount of a castanospermine ester of the formula

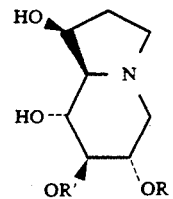

wherein R and R' are independently hydrogen, $C_{1-18}$ alkanoyl, $C_{3-18}$ alkanoyl, and

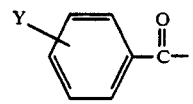

wherein Y is hydrogen, $C_{1-4}$ alkyl, or $C_{1-4}$ alkoxy; with R and R', with the proviso that one of R or R', but not both, must be hydrogen; or a pharmaceutically acceptable salt thereof.

* * * * *